(12) United States Patent
Godfrey

(10) Patent No.: US 6,316,008 B1
(45) Date of Patent: Nov. 13, 2001

(54) COMBINATION OF ZINC IONS AND VITAMIN C AND METHOD OF MAKING

(76) Inventor: John C. Godfrey, 1649 Old Welsh Rd., Huntingdon Valley, PA (US) 19006

(*) Notice: Subject to any disclaimer, the term of this patent is extended or adjusted under 35 U.S.C. 154(b) by 0 days.

(21) Appl. No.: 09/145,975

(22) Filed: Sep. 3, 1998

(51) Int. Cl.$^7$ ................................ A61K 9/00; A61K 9/52; A61K 9/20; A61K 9/22; A61K 47/00

(52) U.S. Cl. .................. 424/400; 424/457; 424/464; 424/468; 424/439; 424/440; 424/441

(58) Field of Search ................................ 424/400, 457, 424/468, 464, 439, 440, 441

(56) References Cited

U.S. PATENT DOCUMENTS

| | | | |
|---|---|---|---|
| 5,326,569 | * 7/1994 | Acosta et al. | 424/440 |
| 5,626,883 | 5/1997 | Paul . | |
| 5,759,559 | 6/1998 | Fitzjarrell . | |
| 5,897,891 | * 4/1999 | Godfrey | 426/74 |

FOREIGN PATENT DOCUMENTS

91/11117   8/1991   (WO) .

OTHER PUBLICATIONS

Patent Abstracts of Japan vol. 012, No. 398 (C–538), Oct. 21, 1988 & JP 63 141921 A (KAO Corp), Jun. 14, 1988 *abstract*.

* cited by examiner

*Primary Examiner*—Thurman K. Page
*Assistant Examiner*—Todd D Ware
(74) *Attorney, Agent, or Firm*—Breiner & Breiner, L.L.C.

(57) ABSTRACT

Compositions for oral use containing at least one zinc compound, at least one amino acid, a source of ascorbic acid which does not appreciably associate with zinc ions, and a base material. The compositions provide for slow release of zinc upon dissolution in the mouth. The amino acid provides the zinc compound(s) with a palatable taste and no aftertaste. The source of ascorbic acid provides Vitamin C without interacting with zinc and forming unpalatable by-products. A method for making such compositions is also described.

20 Claims, No Drawings

COMBINATION OF ZINC IONS AND VITAMIN C AND METHOD OF MAKING

FIELD OF INVENTION

This invention relates to zinc compositions for oral use and methods of making. More particularly, this invention relates to compositions containing a combination of a zinc compound (acting as a source of zinc ions) and a source of ascorbic acid (Vitamin C), which when taken orally are palatable and have no undesirable aftertaste. These compositions include, in addition to the zinc compound and the ascorbic acid source, an amino acid, and a base material.

BACKGROUND OF THE INVENTION

The value of nutritional supplements of elemental zinc is well established. Hypogonadism in males, skin changes, poor appetite, and mental lethargy are but some of the observable effects related to zinc deficiency in man. Approximately 100 enzymes, many of them essential to human well-being, have been found to contain zinc, and the evidence is strong that zinc is required for many (if not all) of these enzymes to express their activity. Several enzymes required for nucleic acid metabolism have been shown to require zinc. In this group are ribonucleic acid (RNA) and deoxyribonucleic acid (DNA) polymerases, deoxythymidine kinase, and reverse transcriptase. It has been shown experimentally that the activity of deoxythymidine kinase in rapidly regenerating connective tissue decreases as early as six days after animals are placed on a zinc-deficient diet. This metabolic defect resulting from nutritional zinc deficiency is an indication of the fundamental importance of zinc for cell division and protein synthesis.

Until recently, zinc deficiency in man was considered unlikely because of the widespread availability of zinc in nature. However, recent evidence suggests that nutritional zinc deficiency may be common among the people of many developing countries where they subsist on high cereal protein diets. Only recently has it been recognized that the phytate content of such diets severely restricts zinc availability, which translates nutritionally to markedly depressed zinc absorption in man under many practical circumstances. Marginal zinc deficiency may be widespread even in the United States because of self-imposed dietary restrictions, use of alcohol and cereal proteins, and the increasing use of refined foods which decrease the intake of trace elements. As meat is a major dietary source of zinc, vegetarians who consume cereals as a major source of protein may be in double jeopardy of zinc deficiency.

Therapeutically, zinc has a vital role in certain diseased or debilitated states. Zinc therapy is life saving in acrodermatitis enteropathica, a genetic disease caused by an autosomal recessive trait which, although rare, had an extremely high mortality rate until it was discovered in 1973 that chronic administration of oral zinc salts was not only life saving but capable of lifetime control of the disease. Zinc supplementation markedly improves wound healing in zinc-deficient individuals. Zinc deficiency is an important feature in many cases of sickle cell anemia characterized by growth retardation and hypogonadism, and zinc appears to have a pharmacological anti-sickling effect. Zinc has also been shown to be beneficial in the relief of acute inflammatory conditions associated with rheumatoid arthritis.

It was found by G. A. Eby, D. R. Davis, and W. W. Halcomb as reported in "Reduction in Duration of Common Colds by Zinc Gluconate Lozenges in a Double-Blind Study," *Antimicrobial Agents and Chemotherapy,* 25(1), pp. 20–24 (1984) that when modest quantities of zinc are slowly ingested by mouth so that the interior surfaces of the mouth and throat are intermittently bathed in a solution of ionic zinc, both the time course and the severity of the symptoms of the common cold are remarkably altered in a favorable way. Their double blind clinical study in 65 humans showed that allowing a tablet containing about 23 mg of elemental zinc, such as zinc gluconate, to slowly dissolve in the mouth once every two hours during 12 to 16 hours a day (the waking hours) reduced the duration of colds from 10.8 days in the untreated group to 3.9 days in the zinc-treated group; and at every time after about one day, the zinc-treated patients had a great reduction in cold symptoms compared to the patients who did not receive zinc.

While the reported observations are highly significant both from the point of view of statistical validity and of the importance of these observations to public health, the authors stated repeatedly in their paper that the disagreeable taste of the zinc gluconate tablets was a serious problem. Many patients receiving zinc gluconate discontinued the treatment on the first day "due to objection to the treatment". The authors stated that "the zinc gluconate lozenges [tablets] we used caused an unexpected unpalatability and distortion of taste in many subjects . . . " and mentioned "the somewhat bitter aftertaste which some people report for zinc gluconate". Furthermore, "unpalatable taste," "distortion of taste," and "mouth irritation" were common objections.

The original observation of the efficacy of unflavored zinc gluconate tablets has received strong confirmation. Two large, double-blind, placebo-controlled clinical studies have been carried out and reported in the medical literature. The first was carried out at the Dartmouth College Cold Clinic in New Hampshire and reported by J. C. Godfrey, B. Conant Sloane, D. S. Smith, J. H. Turco, N. Mercer, and N. J. Godfrey in "Zinc gluconate and the common cold: A controlled clinical study," *Journal of International Medical Research,* 20(2), pp. 234–246 (1992). This study used sugar-based lozenges containing zinc gluconate equivalent to 23 mg of zinc, and glycine, prepared by serial dilution technology to produce a formulation according to U.S. Pat. No. 4,684,528 and 4,758,439. Participants in this study who met protocol requirements and who received active lozenges within two calendar days of the onset of cold symptoms and dissolved them in their mouths every 2 hours while awake, as specified in the protocol carried out under a U.S. Investigational New Drug Application, experienced colds that lasted only 58% (mean duration) as long as patients who received a placebo. Patients in this study who received the active medication also experienced significant reductions of symptom severity and duration as compared to those who received the placebo.

The second double-blind study was done at the Cleveland Clinic Foundation by S. B. Moussad, M. L. Macknin, S. V. Medendork, and P. Mason and reported in "Zinc Gluconate Lozenges for Treating the Common Cold," *Annals of Internal Medicine,* 125(2), pp. 81–88 (1996). Patients who qualified for this study had cold symptoms for no more than 24 hours prior to entry. The study used zinc gluconate lozenges containing glycine, prepared in the same manner as for the Dartmouth study but containing just 13.3 mg of zinc. When the data from this study were analyzed on the same statistical basis as the Dartmouth study, i.e., using only the 83 out of 100 patients who met all criteria specified in the protocol, it was found that patients who took active medication had colds for only 52% as long as those who got a placebo. As in the Dartmouth study, patients in this study also experienced a rapid reduction in symptom severity, compared to those on a placebo.

As noted, zinc gluconate by itself has a very bad taste. This may be overcome by formulations containing an excess of glycine or certain other selected amino acids making the material palatable enough to be taken with the frequency necessary to suppress symptoms of the common cold.

Vitamin C (ascorbic acid) is established as an important nutrient. In view of the long and generally favorable history of the use of Vitamin C as a dietary supplement, antioxidant, and in the treatment of the common cold, it has become apparent that a combination of a zinc supplement with Vitamin C in a single dose lozenge, or similar type oral dosage form is desirable.

However, until now, all attempts to combine zinc compounds with ascorbic acid or ascorbate salts in a lozenge or the like form have failed because of the rapid association of zinc ion with ascorbic acid resulting in a product having a lingering and extremely foul taste. Such foul taste has been found to have a 24 hour staying power. These undesirable characteristics are normally in orders of magnitude stronger than those associated with zinc compounds alone such as zinc gluconate. Further, the addition of an amino acid does not remedy the problem and masking of the zinc ascorbate taste with sugars or flavorants is not successful and is not procedurally or economically practical.

PRIMARY OBJECTS AND GENERAL DESCRIPTION

Accordingly, it is a primary object of the present invention to provide a combination of zinc and ascorbic acid (Vitamin C) for oral usage, which is palatable and which does not have a bad aftertaste.

Another primary object of the invention is to provide an oral supplement including zinc and ascorbic acid in the form of a lozenge or similar oral dosage form.

It is another primary object to provide a method of making the compositions of the present invention.

The above and other objects of the invention will be apparent from the following general description and the detailed examples which follow.

According to the present invention, compositions are described including a zinc salt or salts (as a source of zinc ions), certain sources of ascorbic acid, certain amino acids, and a base material (such as candy or syrup) which are very pleasant to the taste and leave no undesirable aftertaste. Optionally, a minor molecular proportion of a copper salt may be included to eliminate potential adverse effects of excess zinc in the body.

Until now, it has been impractical to uniformly combine ascorbic acid with zinc in a lozenge or like form because of the undesirable taste and aftertaste of the material resulting from the combination. Metal salts generally have been found to readily exchange with zinc ions under conditions of preparation or use, be oxidatively unstable (such as sodium or calcium ascorbate), and not have acceptable taste (e.g., ferric salt which, besides oxidizing the ascorbate, also has a bad iron taste). Surprisingly, two sources of ascorbic acid have been determined which do not have the above drawbacks in the presence of zinc. It has been found that magnesium L-ascorbate (i.e., the magnesium salt of L-ascorbic acid) and L-ascorbyl palmitate are each individually suitable for combination with zinc salts in oral dosage compositions while avoiding the association of zinc ions with ascorbic acid and, thus, avoiding the resulting undesirable flavor therefrom. The magnesium salt of L-ascorbyl palmitate is also suitable for use.

The magnesium salt of L-ascorbic acid is commercially available from SIGMA. L-ascorbyl palmitate is commercially available from Chemical Dynamics Corp.

Amino acids useful in the present invention are monocarboxylic amino acids including glycine, L-alanine, D,L-alanine, L-2-aminobutyric acid, D,L-2-aminobutyric acid, L-valine, D,L-valine, L-isovaline, D,L-isovaline, L-leucine, D,L-leucine, D-isoleucine, D,L-isoleucine, L-lysine, and D,L-lysine. It has also been found that complexes between zinc and the named amino acids having the composition zinc(amino acid)$_2$ are water soluble and have very good flavors when formulated with an excess of the same amino acid, excess being in the range of 2 to 20 moles amino acid per mole of zinc(amino acid)$_2$. Preparations of these complexes are well known. See, e.g., S. Akihama and S. Toyoshima, "Chemotherapeutic Drugs Against Viruses. XXXIV. Antiviral Effects of Zinc Complexes on Japanese B Encephalitis Virus", 10 *Chem. Pharm. Bull.* 1254–57 (1962); B. W. Low, F. K. Hirshfeld, and F. M. Richards, "Glycinate Complexes of Zinc and Cadmium", 81 *J. Am. Chem. Soc.* 4412–16 (1959). It has further been found that certain other amino acids, such as the dicarboxylic amino acids aspartic and glutamic acids, are not useful for this purpose. Mixtures of amino acids may also be used.

Zinc compounds useful in combination with the amino acid and the ascorbic acid source can be in any of the forms commonly used, such as the sulfate, carbonate, chloride, acetate, gluconate, citrate, aspartate, picolinate, orotate, and transferrin salts, as well as zinc oxide and complexes of divalent zinc with the amino acids. Mixtures of zinc salts may also be used.

The base material which can be used as a carrier for the zinc compound, amino acid, and source of ascorbic acid can be a sweetening agent such as a soft or hard candy base. Alternatively, a syrup such as corn syrup, or a gum material such as chewing gum may be used. Any form which permits the oral intake of the zinc/ascorbic acid combination and particularly where the composition is retained in the mouth for a substantial period of time to permit prolonged contact in the mouth with the zinc to provide a slow release of zinc into the mouth may be used. Preferably, the base material is a hard or soft candy base optionally containing a flavoring agent such as a fruit flavor concentrate or a syrup such as a natural or artificially sweetened syrup.

The composition of the present invention may also optionally include a minor proportion relative to zinc (about 0.01 to 0.1 molar equivalents) of a copper salt such as the sulfate, chloride, acetate, gluconate, ascorbate, citrate, aspartate, carbonate, picolinate, orotate and transferrin salts, as well as cupric oxide and complexes of divalent copper with amino acids.

Suitable ratio ranges for use in the composition of the present invention include approximately 2 to 20 moles of amino acid(s) per mole of zinc ions (i.e., zinc compound), and approximately 0.01 to 0.10 mole of cupric ions per mole of zinc ions. The ascorbic acid or equivalent is present based on the source of ascorbic acid in an amount of about 30–300 mg per 4.5 g of lozenge. It is noted that in view of the ascorbate sources, it is technically difficult to make lozenges with much more than 120 mg of ascorbic acid (or equivalent) per 4.5 g of lozenge. The lozenges of the present invention most preferably contain approximately 0.2 mmol zinc in the form of zinc gluconate, approximately 0.35 mmol ascorbic acid in the form of magnesium L-ascorbate or L-ascorbyl palpitate, approximately 2.0 mmol glycine, and a hard candy base of approximately 4.5 g. These amounts may also be scaled up to produce a larger or a smaller lozenge.

DESCRIPTION OF PRESENTLY PREFERRED EMBODIMENTS

The following examples of presently preferred embodiments serve to illustrate, but not to limit, the present invention.

In preparing the composition of the invention, it is understood that magnesium ascorbate is $C_{12}H_{14}O_{12}Mg$ with a molecular weight of 374.53. The ascorbic acid salt as commercially available, however, is 95% active. The ascorbic acid anion has a mol. wt. of 175.11 and it is desired, in the specific examples set forth and generally, to place an equivalent of 60 mg of pure ascorbic acid in one 4.5 g lozenge. Thus, in correcting for the 95% purity of magnesium ascorbate, each 4.5 g lozenge will contain 68 mg of magnesium ascorbate (95%). Zinc will be present as 104 mg of zinc gluconate trihydrate in the 4.5 g lozenge of the examples. Further, 153 mg (i.e., 10 molar equivalents as compared to the zinc ions) of glycine will be present in each 4.5 g lozenge of the examples. The hard candy base will make up 4.175 g of the 4.5 g lozenge.

Preparation of Unflavored Hard Candy Base

A mixture of 360 g sucrose, 40 g fructose, 160 ml light KARO corn syrup, and 160 ml water in a Teflon-lined 2-quart aluminum pan was brought to a boil while stirring until the temperature of the mixture reached 212° F. Heating was continued without stirring until the temperature reached 300° F. The mixture was then poured into a lightly lubricated (e.g., with a cooking spray such as PAM®) aluminum pan, cooled to room temperature, and fractured into smaller pieces. The pieces were stored at room temperature in a sealed container.

EXAMPLE 1

Zinc Lozenges Containing Magnesium Ascorbate

First, a zinc gluconate glycine concentrate was prepared. A mixture of 61.2 g glycine and 41.6 g zinc gluconate trihydrate was ground together in a grinder to a very fine zinc gluconate/glycine (ZGG) powder.

A mixture of 25.7 g ZGG and 6.8 g magnesium L-ascorbate (95% purity) (SIGMA No. A-0322, Lot 65H2657) was ground to a fine powder in a grinder.

200 g hard candy base (HCB) was heated in an aluminum pan at 220° F. for 40 minutes to convert it to a mobile syrup. To this was added 15.6 g of the ZGG/magnesium ascorbate powder. After stirring, this mixture was spread onto a lightly greased aluminum sheet and pressed to form a 6" diameter disc or "cookie". A knife was used to score the disc-shaped material as it cooled into approximately 4 g to 5 g square lozenges. Upon cooling, the material was broken up into 41 opaque, slightly cream colored, off-white lozenges, average weight 4.5 g. This product contained 2.97 mg of $Zn^{2+}$ and 13.45 mg of ascorbic acid per gram (equivalent). It also contained 0.93 mg of $Mg^{2+}$ per gram, from the magnesium ascorbate.

The resulting lozenges were found to have a pleasant flavor, strong zinc ion astringency, and a slight grittiness. No trace of bad taste due to zinc ion-ascorbic acid interaction was detected nor was there any bad aftertaste. No change was detected upon reevaluation after 15 days, and after 5 months storage at room temperature in a sealed container. Thus, it is clear that no exchange of $Zn^{2+}$ for $Mg^{2+}$ occurred in this formulation, for if such exchange had occurred, the well-established foul taste of zinc ascorbate would have been readily detectable.

EXAMPLE 2

Zinc Lozenge with Ascorbyl Palmitate

L-ascorbyl palmitate as used herein is as commercially available from Chemical Dynamics Corp., Product No. 08-380-000. L-ascorbyl palmitate has a molecular weight of 414.53. Ascorbate ion has a molecular weight of 175.11.

In the example set forth below, it is desired to place 60 mg of ascorbic acid from L-ascorbyl palmitate into a 4.5 g lozenge together with 13.3 mg zinc ion from 104 mg of zinc gluconate trihydrate and 153 mg (10 molar equivalents relative to the zinc) of glycine. Thus, one lozenge of the example will include 158 mg of 90% L-ascorbyl palmitate, 104 mg zinc gluconate trihydrate, 153 mg glycine, and 4.085 g of HCB.

A mixture of 25.7 g ZGG and 15.8 g L-ascorbyl palmitate (LAP) was ground together to a fine powder in a grinder.

204.2 g HCB was heated at 220° F. for 45 min. to give a free-flowing syrup. To this was added 20.8 g of the ZGG/LAP powder with stirring. This mixture was stirred to produce a uniform, white taffy-like material.

This material was transferred to a lightly lubricated or greased aluminum pan, spread out to form a 6" disc or "cookie", and scored into square lozenges as it cooled. The disc was broken into approximately 4 g to 5 g lozenges.

The resultant lozenges were found to have a pleasant taste, be notably astringent, and have no aftertaste. There was a slight "waxy" feel in the mouth, especially on the occlusal surfaces of the teeth, due to the palmitic acid moiety of the LAP. The taste noticeably improved after 2 days storage at room temperature and was entirely stable for at least five months. Thus, it is clear that no hydrolysis of the palmitate ester occurred under the conditions of this preparation, for if such hydrolysis had occurred, there would have been some metathesis to zinc ascorbate, readily detectable by its foul taste.

As will be apparent to one skilled in the art, various modifications can be made within the scope of the aforesaid description. Such modifications being within the ability of one skilled in the art form a part of the present invention and are embraced by the appended claims.

It is claimed:

1. A slow release composition for oral consumption comprising a base material uniformly containing at least one zinc compound, at least one mono-carboxylic amino acid present in an excess molar amount as to said at least one zinc compound, and an ascorbic acid compound selected from the group consisting of ascorbyl esters and magnesium ascorbate, wherein zinc is slowly and uniformly released as the composition is orally consumed.

2. A slow release composition for oral consumption produced by combining a base material, at least one zinc compound, at least one mono-carboxylic amino acid present in an excess molar amount as to said at least one zinc compound, and an ascorbic acid compound selected from the group consisting of ascorbyl esters and magnesium ascorbate, wherein zinc is slowly and uniformly released as the composition is orally consumed.

3. The composition of claim 1 or 2 wherein said ascorbic acid compound L-ascorbyl palmitate.

4. The composition of claim 1 or 2 wherein said ascorbyl esters include a magnesium salt of L-ascorbyl palmitate.

5. The composition of claim 1 or 2 further comprising a copper compound.

6. The composition of claim 1, wherein said at least one amino acid is selected from the group consisting of glycine, L-alanine, D,L-alanine, L-2-aminobutyric acid, D,L-2-aminobutyric acid, L-valine, D,L-valine, L-isovaline, D,L-isovaline, L-leucine, D,L-leucine, D-isoleucine, D,L-isoleucine, L-lysine, and D,L-lysine.

7. The composition of claim 1, wherein said at least one zinc compound is a zinc salt in the form of a sulfate, carbonate, chloride, acetate, gluconate, citrate, aspartate, picolinate, orotate, and transferrin salt.

8. The composition of claim 1, wherein said at least one amino acid is glycine.

9. The composition of claim 1, wherein said at least one zinc compound is a complex of divalent zinc with said amino acid.

10. The composition of claim 1, wherein said at least one zinc compound is zinc gluconate.

11. The composition of claim 1, wherein said at least one zinc compound is zinc acetate.

12. The composition of claim 1, wherein said at least one zinc compound is zinc citrate.

13. The composition of claim 1 or 2, wherein said composition comprises an oral dosage form of about 2 g to 10 g in mass.

14. The composition of claim 1 or 2, wherein said ascorbic acid compound is present in an amount relative to zinc of about 1 to 2 molar equivalents.

15. The composition of claim 5, wherein said copper compound is selected from the group consisting of cupric L-alaninate, cupric carbonate, cupric chloride, cupric citrate, cupric gluconate, cupric gylcinate, cupric oxide, cupric salicylate, and cupric tartrate.

16. The composition of claim 1 or 2, wherein said at least one amino acid is present to said at least one zinc compound in a ratio range of approximately 2 to 20 moles of amino acid for each one mole of said at least one zinc compound, and ascorbic acid is present based on said ascorbic acid compound in an amount of 30 to 300 mg per 4.5 g of lozenge.

17. The composition of claim 5, wherein said at least one amino acid is present to said at least one zinc compound in a ratio range of approximately 2 to 20 moles of amino acid for each one mole of said at least one zinc compound, said copper compound is present to said at least one zinc compound in a molar ratio of 0.01 to 0.10 mole of said copper compound for each one mole of said at least one zinc compound, and ascorbic acid is present based on said ascorbic acid compound in an amount of 30 to 300 mg per 4.5 g of lozenge.

18. A method of preparing a composition according to claim 1 or 2 comprising:

combining said at least one zinc compound and said at least one amino acid to form a first mixture;

combining said first mixture with said ascorbic acid compound to form a second mixture;

heating said base material and combining said base material with said second mixture to form a third mixture;

forming the third mixture into an oral dosage form; and allowing said oral dosage form to cool.

19. The method of claim 18 wherein said ascorbic acid compound is present in an amount relative to said zinc of about 1 to 2 molar equivalents.

20. The method of claim 18 wherein said at least one amino acid is present to said at least one zinc compound in a ratio range of approximately 2 to 20 moles of amino acid for each mole of said at least one zinc compound.

\* \* \* \* \*

UNITED STATES PATENT AND TRADEMARK OFFICE
CERTIFICATE OF CORRECTION

Page 1 of 1

PATENT NO. : 6,316,008 B1
DATED : November 13, 2001
INVENTOR(S) : John C. Godfrey It is certified that error appears in the above-identified patent and that said Letters Patent is hereby corrected as shown below:

<u>Column 6, claim 3,</u>
Line 55, after "compound" insert -- is --.

Signed and Sealed this

Nineteenth Day of March, 2002

Attest:

Attesting Officer

JAMES E. ROGAN
Director of the United States Patent and Trademark Office